(12) United States Patent
Murayama et al.

(10) Patent No.: US 7,922,673 B2
(45) Date of Patent: Apr. 12, 2011

(54) GUIDE WIRE

(75) Inventors: Hiraku Murayama, Fujinomiya (JP); Akihiko Umeno, Fujinomiya (JP); Jun Iwami, Fujinomiya (JP); Yutaka Itou, Fujinomiya (JP); Youki Aimi, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 847 days.

(21) Appl. No.: 10/635,712

(22) Filed: Aug. 7, 2003

(65) Prior Publication Data
US 2004/0039309 A1   Feb. 26, 2004

(30) Foreign Application Priority Data

Aug. 23, 2002 (JP) ................. 2002-244316
Dec. 6, 2002 (JP) ................. 2002-355907
May 30, 2003 (JP) ................. 2003-156010

(51) Int. Cl.
*A61B 5/00* (2006.01)
*A61M 25/00* (2006.01)
(52) U.S. Cl. ................................. 600/585
(58) Field of Classification Search .......... 600/433, 600/434, 585; 604/164.01, 164.13
See application file for complete search history.

(56) References Cited

U.S. PATENT DOCUMENTS

| | | | |
|---|---|---|---|
| 4,925,445 A | 5/1990 | Sakamoto et al. | |
| 5,100,430 A * | 3/1992 | Avellanet et al. | 606/205 |
| 5,111,829 A | 5/1992 | Alvarez de Toledo | |
| 5,171,383 A | 12/1992 | Sagae et al. | |
| 5,341,817 A | 8/1994 | Viera | |
| 5,341,818 A | 8/1994 | Abrams et al. | |
| 5,358,796 A | 10/1994 | Nakamura et al. | |
| 5,365,943 A | 11/1994 | Jansen | |
| 5,368,661 A | 11/1994 | Nakamura et al. | |
| 5,409,015 A | 4/1995 | Palermo | |
| 5,411,476 A | 5/1995 | Abrams et al. | |
| 5,465,733 A * | 11/1995 | Hinohara et al. | 600/585 |
| 5,636,641 A | 6/1997 | Fariabi | |

(Continued)

FOREIGN PATENT DOCUMENTS

EP   0 473 790 A1   3/1992

(Continued)

OTHER PUBLICATIONS

U.S. Appl. No. 10/634,845, filed Aug. 2003, Murayama et al.*

(Continued)

*Primary Examiner* — Max Hindenburg
*Assistant Examiner* — Jonathan M Foreman
(74) *Attorney, Agent, or Firm* — Buchanan Ingersoll & Rooney PC

(57) ABSTRACT

A guide wire includes a first wire disposed on the distal side of the guide wire and a second wire disposed on the proximal side from the first wire. The first wire and the second wire are joined to each other by welding. A welded portion formed by welding has a projection projecting in the outer peripheral direction. The height of the projection may be in a range of 0.001 to 0.3 mm. The first wire may be made from a superelastic alloy, and the second wire be made from a stainless steel. The first wire and the second wire are welded to each other by a butt resistance welding process. Such a guide wire has a high joining strength between the first wire and the second wire, to thereby improve the operationality.

25 Claims, 12 Drawing Sheets

U.S. PATENT DOCUMENTS

| | | | |
|---|---|---|---|
| 5,636,642 A | 6/1997 | Palermo | |
| 5,637,089 A | 6/1997 | Abrams et al. | |
| 5,695,111 A | 12/1997 | Nanis et al. | |
| 5,701,911 A | 12/1997 | Sasamine et al. | |
| 5,720,300 A | 2/1998 | Fagan et al. | |
| 5,749,837 A | 5/1998 | Palermo et al. | |
| 5,769,796 A | 6/1998 | Palermo et al. | |
| 5,772,609 A | 6/1998 | Nguyen et al. | |
| 5,813,997 A * | 9/1998 | Imran et al. | 600/585 |
| 5,865,768 A * | 2/1999 | Orr | 600/585 |
| 5,938,623 A * | 8/1999 | Quiachon et al. | 600/585 |
| 5,957,865 A * | 9/1999 | Backman et al. | 600/585 |
| 5,980,471 A * | 11/1999 | Jafari | 600/585 |
| 6,001,068 A | 12/1999 | Uchino et al. | |
| 6,019,737 A | 2/2000 | Murata | |
| 6,039,700 A | 3/2000 | Sauter | |
| 6,139,510 A | 10/2000 | Palermo | |
| 6,165,292 A | 12/2000 | Abrams et al. | |
| 6,196,964 B1 | 3/2001 | Loffler et al. | |
| 6,203,485 B1 | 3/2001 | Urick | |
| 6,210,312 B1 | 4/2001 | Nagy | |
| 6,234,981 B1 | 5/2001 | Howland | |
| 6,248,082 B1 | 6/2001 | Jafari | |
| 6,390,993 B1 * | 5/2002 | Cornish et al. | 600/585 |
| 6,488,637 B1 | 12/2002 | Eder et al. | |
| 6,492,037 B2 | 12/2002 | Shindo et al. | |
| 6,692,841 B2 | 2/2004 | Shindo et al. | |
| 2001/0011158 A1 | 8/2001 | Howland | |
| 2001/0023319 A1 | 9/2001 | Miyata et al. | |
| 2003/0069521 A1 * | 4/2003 | Reynolds et al. | 600/585 |
| 2003/0100847 A1 * | 5/2003 | D'Aquanni et al. | 600/585 |

FOREIGN PATENT DOCUMENTS

| | | | |
|---|---|---|---|
| EP | 0 774 186 | | 11/1996 |
| EP | 0 838 230 A2 | | 4/1998 |
| JP | 1-124473 | | 5/1989 |
| JP | 03089426 A | * | 4/1991 |
| JP | 04-009162 A | | 1/1992 |
| JP | 04-292174 A | | 10/1992 |
| JP | 06-047570 A | | 2/1994 |
| JP | 06-063151 A | | 3/1994 |
| JP | 08-004727 A | | 1/1996 |
| JP | 8-19883 | | 1/1996 |
| JP | 08-084776 A | | 4/1996 |
| JP | 10-033689 A | | 2/1998 |
| JP | 10-057499 A | | 3/1998 |
| JP | 10-118005 A | | 5/1998 |
| JP | 10-179758 A | | 7/1998 |
| JP | 10-328157 A | | 12/1998 |
| JP | 11-000737 A | | 1/1999 |
| JP | 11-057014 A | | 3/1999 |
| JP | 11-57041 | | 3/1999 |
| JP | 11-151578 A | * | 6/1999 |
| JP | 11-151578 A | | 6/1999 |
| JP | 11-176268 | | 7/1999 |
| JP | 2000-514326 A | | 10/2000 |
| JP | 2002-78805 | | 3/2002 |
| JP | 2002-534167 A | | 10/2002 |
| JP | 2003-159333 A | | 6/2003 |
| WO | WO 01/36034 A2 | | 5/2001 |
| WO | WO 03/030982 A2 | | 4/2003 |

OTHER PUBLICATIONS

U.S. Appl. No. 10/635,716, filed Aug. 2003, Murayama et al.*
Notice of Reasons for Refusal issued in Japanese Application No. 2003-156010 and English language translation.
Notice of Reasons for Refusal issued in Japanese Application No. 2002-354233 and English language translation.

* cited by examiner

F I G. 2 A
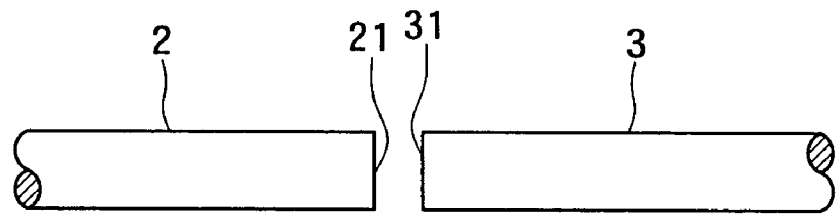
F I G. 2 B
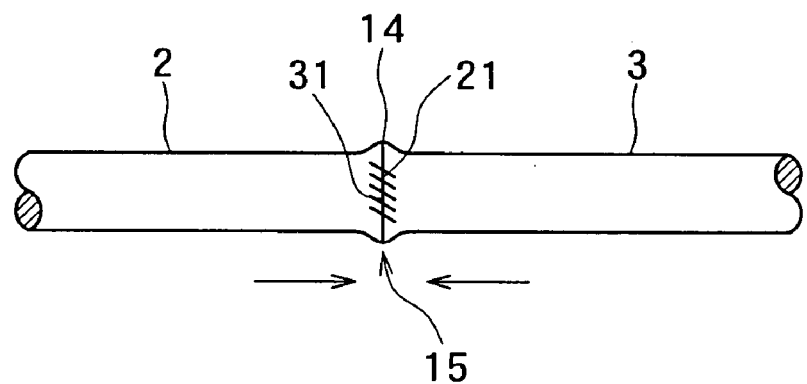
F I G. 2 C
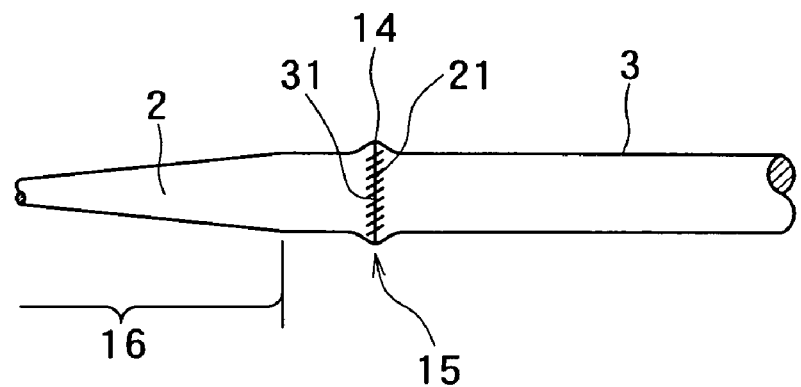

GUIDE WIRE

BACKGROUND OF THE INVENTION

1. Field of the Invention

The present invention relates to a guide wire, particularly to a guide wire used to guide a catheter in a body lumen such as a blood vessel.

2. Description of the Related Art

Guide wires are used to guide a catheter in treatment of cites at which open surgeries are difficult or which require minimally invasiveness to the body, for example, PTCA (Percutaneous Transluminal Coronary Angioplasty), or in examination such as cardio-angiography. A guide wire used in the PTCA procedure is inserted, with the distal end projecting from the distal end of a balloon catheter, into the vicinity of a target angiostenosis portion together with the balloon catheter, and is operated to guide the distal end portion of the balloon catheter to the target angiostenosis portion.

A guide wire used to insert a catheter into a blood vessel complicatedly bent requires appropriate flexibility and restoring performance against bending, pushability and torque transmission performance (generically called "operationality") for transmitting an operational force from the proximal end portion to the distal side, and kink resistance (often called "resistance against sharp bending"). To obtain appropriate flexibility as one of the above-described performances, there has been known a guide wire configured such that a metal coil having flexibility is provided around a small-sized core member at the distal end of the guide wire, or a guide wire including a core member made from a superelastic material such as an Ni—Ti alloy for improving the flexibility and restoring performance.

Conventional guide wires include a core member that is substantially made from a single material. In particular, to enhance the operationality of the guide wire, a material having a relatively high elastic modulus is used as the material of the core member. The guide wire including such a core member, however, has an inconvenience that the distal end portion of the guide wire becomes lower in flexibility. On the other hand, if a material having a relatively low elastic modulus is used as the material of the core member for increasing the flexibility of the distal end portion of the guide wire, the operationality of the proximal end portion of the guide wire is degraded. In this way, it has been regarded as difficult to satisfy both requirements associated with the flexibility and operationality by using a core member made from a single material.

A guide wire intended to solve such a problem has been disclosed, for example, in U.S. Pat. No. 5,171,383, wherein a Ni—Ti alloy wire is used as a core member, and the distal side and the proximal side of the alloy wire are heat-treated under different conditions in order to enhance the flexibility of the distal end portion of the alloy wire while enhancing the rigidity of the proximal side of the alloy wire. Such a guide wire, however, has a problem that the control of the flexibility of the distal end portion by heat-treatment has a limitation. For example, even if it is successful to obtain a sufficient flexibility of the distal end portion of the alloy wire, it may often fail to obtain a sufficient rigidity on the proximal side of the alloy wire.

SUMMARY OF THE INVENTION

An object of the present invention is to provide a guide wire capable of improving the strength of a joining portion between a first wire on the distal side and a second wire on the proximal side, thereby enhancing the operationality of the guide wire.

To achieve the above object, according to a first aspect of the present invention, there is provided a guide wire including a first wire disposed on the distal side of the guide wire, and a second wire disposed on the proximal side from the first wire, wherein the first wire and the second wire are joined to each other by welding, and a welded portion formed by welding has a projection projecting in the outer peripheral direction.

According to a second aspect of the present invention, there is provided a guide wire including a first wire disposed on the distal side of the guide wire, and a second wire disposed on the proximal side from the first wire, the second wire having a rigidity higher than that of the first wire, wherein the first wire and the second wire are joined to each other by welding, a welded portion formed by welding has a projection projecting in the outer peripheral direction, the second wire has a first portion provided in the vicinity of the distal end of the second wire and a second portion provided on the proximal side from the first portion, and the first portion has a rigidity lower than that of the second portion.

Each of the guide wires according to the first and second aspects of the present invention may be further configured as follows.

The guide wire may further include a cover layer disposed over at least the welded portion.

The projection may be visible under fluoroscopy.

The guide wire may further include a spiral coil covering at least a distal end portion of the first wire.

The proximal end of the coil may abut on the projection.

The height of the projection may be in a range of 0.01 to 0.3 mm.

The welding is performed by a butt resistance welding process.

Each of the connection end face of the first wire to the second wire and the connection end face of the second wire to the first wire may be nearly perpendicular to the axial direction of the first and second wires.

The guide wire may have an outer-diameter gradually reducing portion with its outer diameter gradually reduced in the direction toward the distal end.

The outer-diameter gradually reducing portion may be provided on the distal side from the welded portion.

The outer-diameter gradually reducing portion may be provided on the proximal side from the welded portion.

The first wire has an outer diameter being nearly constant over the entire length except for the projection.

The first wire may be made from a material having an elastic modulus smaller than that of the second wire.

The first wire may be made from a superelastic alloy.

The second wire may be made from a stainless steel.

The second wire may be made from a Co-based alloy.

The Co-based alloy may be a Co—Ni—Cr alloy.

The guide wire may have at least one projection projecting in the outer peripheral direction in addition to the projection provided at the welded portion.

The proximal side and the distal side of the projection may be formed into shapes asymmetric to each other with respect to the welded surface of the welded portion.

A portion, located in the vicinity of the welded portion between the first wire and the second wire may have e thinned portion, and the projection may be provided on the thinned portion.

As described above, according to the present invention, by providing the first wire disposed on the distal side and the second wire disposed on the proximal side from the first wire, it is possible to provide a guide wire having good operationality. In particular, by providing the first wire having a high flexibility and the second wire made from a material having an elastic modulus larger than that of the first wire, it is possible to provide a guide wire having the distal end portion having a high flexibility and the proximal end portion having a high rigidity, thereby improving the pushing performance, torque transmission performance, and trackability.

Since the first wire and the second wire are joined to each other by welding and the projection is formed at the welded portion, it is possible to the joining strength of the joining portion (welded portion), and hence to certainly transmit a torsional torque and a pushing force from the second wire to the first wire.

Since the projection is provided at the welded portion between the first wire and the second wire, the welded portion becomes easily visible under fluoroscopy, to improve the operationality of the guide wire and a catheter used together with the guide wire, thereby shortening the operation time and improving the safety.

The provision of the projection is also effective in reducing the contact area of the guide wire with the inner wall of a catheter used together with the guide wire, to reduce the friction resistance of the guide wire during movement of the guide wire relative to the catheter, thereby improving the sliding performance. As a result, it is possible to enhance the operationality of the guide wire in the catheter.

In the case of providing the cover layer made from a material capable of reducing the friction, it is possible to improve the sliding performance of the guide wire in the catheter, thereby further enhancing the operationality of the guide wire. Since the sliding resistance of the guide wire is reduced, it is possible to more certainly prevent kink (sharp bending) or torsion, especially, of a portion in the vicinity of the welded portion.

By changing materials used for the cover layer at respective portions, it is possible to enhance the sliding resistance at each of the portions and hence to expand the versability for an operator.

BRIEF DESCRIPTION OF THE DRAWINGS

These and other objects, features, and advantages of the present invention will become more apparent from the following detailed description in conjunction with the accompanying drawings, wherein:

FIGS. 2A to 2C are views showing steps of a procedure for connecting a first wire and a second wire of the guide wire shown in FIG. 1;

DETAILED DESCRIPTION OF THE PREFERRED EMBODIMENTS

A guide wire of the present invention will now be described in detail by way of preferred embodiments shown in the accompanying drawings.

Figure 1:
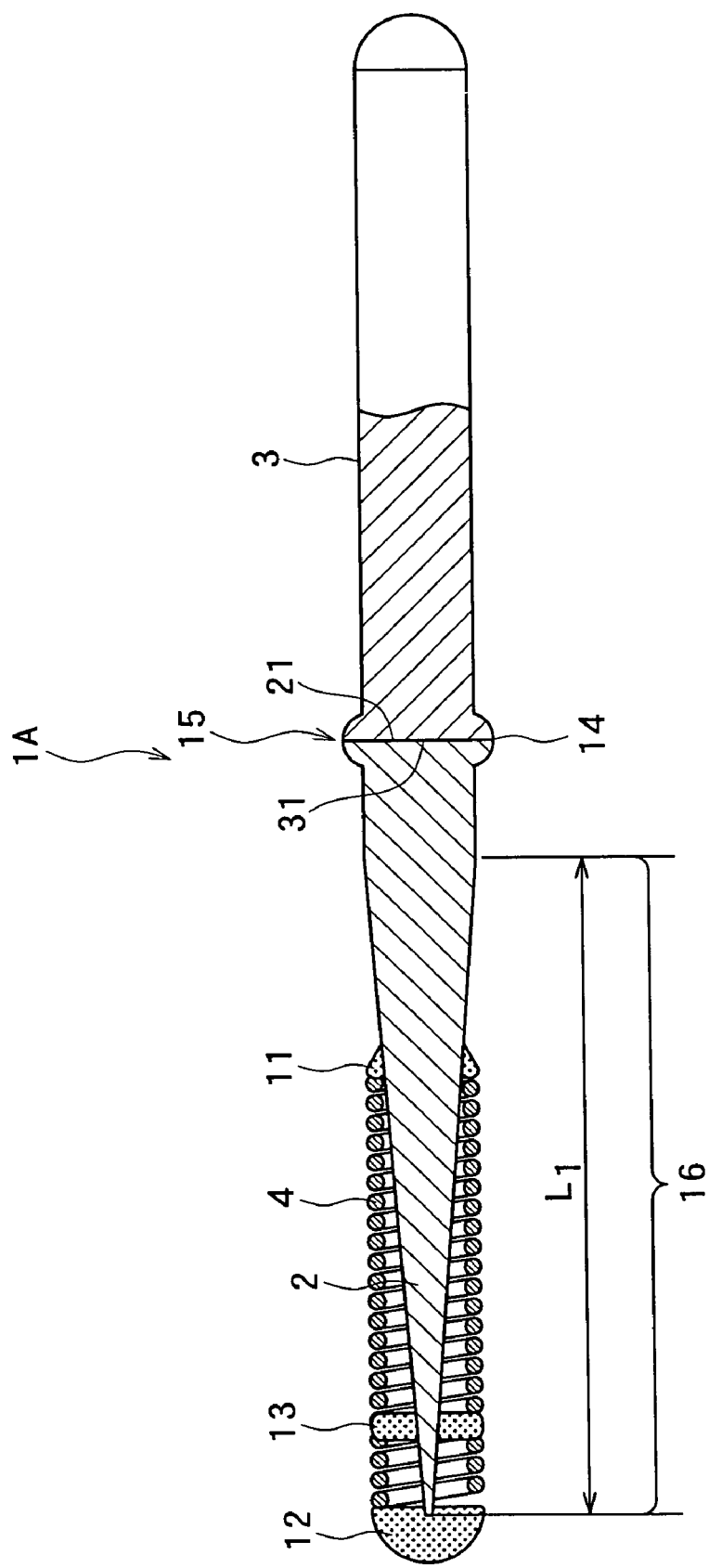
FIG. 1 is a longitudinal sectional view showing a first embodiment of a guide wire of the present invention.

FIG. 1 is a longitudinal sectional view of a first embodiment of a guide wire of the present invention, and FIGS. 2A to 2C are views showing a procedure for joining a first wire and a second wire of the guide wire shown in FIG. 1 to each other. For convenience of description, the right side in FIG. 1 is taken as the "proximal side" and the left side in FIG. 1 is taken as the "distal side". It is to be noted that in FIG. 1 and FIGS. 2A to 2C (and in FIGS. 5 to 9 to be described later), for easy understanding, the dimension of the guide wire in the thickness direction is exaggeratedly enlarged while the dimension of the guide wire in the length direction is shortened, and therefore, the ratio of the thickness to the length is significantly different from the actual ratio.

A guide wire 1A shown in FIG. 1, which is of a type used to be inserted in a catheter, includes a first wire 2 disposed on the distal side, a second wire 3 disposed on the proximal side from the first wire 2, and a spiral coil 4. The entire length of the guide wire 1A is not particularly limited but is preferably in a range of about 200 to 5,000 mm. The outer diameter of the guide wire 1A is not particularly limited but is preferably in a range of about 0.2 to 1.2 mm.

The first wire 2 is configured as a wire member having elasticity. The length of the first wire 2 is not particularly limited but is preferably in a range of about 20 to 1,000 mm.

According to this embodiment, the first wire 2 has an outer-diameter gradually reducing portion 16 with its outer diameter gradually reduced in the direction toward the distal end. This gradually reduces the rigidity (flexural rigidity, torsional rigidity) of the first wire 2 in the direction toward the distal end. As a result, the distal end portion of the guide wire 1A has a high flexibility, to improve trackability and safety to a blood vessel and to prevent sharp-bending and the like.

The length of the outer-diameter gradually reducing portion 16 (denoted by character $L_1$ in FIG. 1) is not particularly limited but is preferably in a range of about 10 to 1,000 mm, more preferably, about 20 to 300 mm. By setting the length $L_1$ in the above range, the change in rigidity in the longitudinal direction becomes more moderate (or smooth).

According to this embodiment, the outer-diameter gradually reducing portion 16 is tapered such that the outer diameter is continuously reduced with a nearly constant reduction ratio in the direction toward the distal end. In other words, the taper angle of the outer-diameter gradually reducing portion 16 is kept nearly constant along the longitudinal direction. In the guide wire 1A according to this embodiment, therefore, the change in rigidity becomes more moderate (or smooth) along the longitudinal direction. Unlike such a configuration, the reduction ratio of the outer diameter of the outer-diameter gradually reducing portion 16 (taper angle of the outer-diameter gradually reducing portion 16) may be changed along the longitudinal direction. For example, portions in each of which the reduction ratio of the outer diameter is relatively large and portions in each of which the reduction ratio of the outer diameter is relatively small may be alternately repeated by a plurality of numbers. In this case, the outer-diameter gradually reducing portion 16 may have a portion in which the reduction ratio of the outer diameter in the direction toward the distal end becomes zero.

The material for forming the first wire 2 is not particularly limited but may be selected from metal materials, for example, stainless steels such as SUS304, SUS303, SUS316, SUS316L, SUS316J1, SUS316J1L, SUS405, SUS430, SUS434, SUS444, SUS429, SUS430F, and SUS302 and alloys having pseudo-elasticity, for example, superelastic alloys. Of these materials, superelsatic alloys are preferable. Superelastic alloys are relatively flexible, good in restoring performance, and no or less plastic deforming. Accordingly, if the first wire 2 is made from a superelastic alloy, the guide wire 1A including such a first wire 2 has, at its distal portion, a high flexibility and a high restoring performance against bending, and a high trackabiligy to a blood vessel complicatedly curved or bent, to thereby enhance the operationality of the guide wire 1A. Even if the first wire 2 is repeatedly deformed, that is, curved or bent, the first wire 2 is no or less plastic deforming because of its high restoring performance. This prevents degradation of the operationality due to the plastic deforming of the first wire 2 during use of the guide wire 1A.

Pseudo-elastic alloys include those of a type in which the stress-strain curve in a tensile test has any shape, those of a type in which a transformation point such as As, Af, Ms, or Mf can be significantly measured or not measured, and all of a type in which the shape is greatly deformed by stress and then restored nearly to an original shape by removal of stress.

Examples of superelastic alloys include Ni—Ti alloys such as an Ni—Ti alloy containing Ni in an amount of 49-52 atomic %, a Cu—Zn alloy containing Zn in an amount of 38.5 to 41.5 wt %, a Cu—Zn—X alloy containing X in an amount of 1 to 10 wt % (X: at least one kind selected from a group consisting of Be, Si, Sn, Al, and Ga), and an Ni—Al alloy containing Al in an amount of 36 to 38 atomic %. Of these materials, the Ni—Ti alloy is preferable.

The distal end of the second wire 3 is joined to the proximal end of the first wire 2. The second wire 3 is a wire member having elasticity. The length of the second wire 3 is not particularly limited but may be in a range of about 20 to 4,800 mm.

The second wire 3 is generally made from a material having an elastic modulus (Young's modulus or modulus of longitudinal elasticity, modulus of rigidity or modulus of transverse elasticity, or bulk modulus) different from that of the first wire 2. The guide wire 1A obtained by joining the first wire 2 and the second wire 3 different in elastic modulus to each other exhibits desired operationality.

The material for forming the second wire 3 is not particularly limited but may be selected from metal materials, for example, stainless steels (all kinds specified in SUS, for example, SUS304, SUS303, SUS316, SUS316L, SUS316J1, SUS316J1L, SUS405, SUS430, SUS434, SUS444, SUS429, SUS430F, and SUS302), piano wire steels, cobalt alloys, and alloys having pseudo-elasticity.

In particular, cobalt alloys are preferably used for the second wire 3. This is because the second wire 3 made from a cobalt alloy has a high elastic modulus and an appropriate elastic limit. Such a second wire 3 exhibits a high torque transmission performance, thereby hardly causing a problem associated with buckling or the like. Any type of cobalt alloy may be used insofar as it contains cobalt. In particular, a cobalt alloy containing cobalt as a main component (that is, a cobalt-based alloy containing cobalt in an amount [in wt %] being the largest among the contents of all components of the alloy) is preferably used, and further, a Co—Ni—Cr alloy is more preferable. The use of the cobalt alloy having such a composition as the material for forming the second wire 3 is effective to further enhance the above-described effects. The cobalt alloy having such a composition is also advantageous in that since the alloy exhibits plasticity in deformation at room temperature, the second wire 3 made from such a cobalt alloy is easily deformable into a desired shape, for example, during use of the guide wire. A further advantage of the cobalt alloy having such a composition is as follows: namely, since the second wire 3 made from such a cobalt alloy has a high elastic modulus and is cold-formable even if it exhibits a high elastic limit, the second wire 3 can be thinned while sufficiently preventing occurrence of buckling, and therefore, can exhibit a high flexibility and a high rigidity enough to be inserted into a desired site.

The Co—Ni—Cr alloy is exemplified by an alloy containing 28-50 wt % of Co, 10-30 wt % of Ni, and 10-30 wt % of Cr, the balance being Fe. In this alloy, part of any component may be substituted by another element (substitution element). The incorporation of such a substitution element exhibits an effect inherent to the kind thereof. For example, the incorporation of at least one kind selected from a group consisting of Ti, Nb, Ta, Be, and Mo further improves the strength of the second wire 3. In the case of incorporating one or more substitution elements other than Co, Ni, and Cr, the total content of the substitution elements is preferably in a range of 30 wt % or less.

For example, part of Ni may be substituted by Mn, which is effective to further improve the workability. Part of Cr may be substituted by Mo and/or W, which is effective to further improve the elastic limit. Of the Co—Ni—Cr alloys, a Co—Ni—Cr—Mo alloy is particularly preferable.

Examples of compositions of the Co—Ni—Cr alloys include (1) 40 wt % Co-22 wt % Ni-25 wt % Cr-2 wt % Mn-0.17 wt % C-0.03 wt % Be—Fe (balance), (2) 40 wt % Co-15 wt % Ni-20 wt % Cr-2 wt % Mn-7 wt % Mo-0.15 wt % C-0.03 wt % Be—Fe (balance), (3) 42 wt % Co-13 wt % Ni-20 wt % Cr-1.6 wt % Mn-2 wt % Mo-2.8 wt % W-0.2 wt % C-0.04 wt % Be—Fe (balance), (4) 45 wt % Co-21 wt % Ni-18 wt % Cr-1 wt % Mn-4 wt % Mo-1 wt % Ti-0.02 wt % C-0.3 wt % Be—Fe (balance), and (5) 34 wt % Co-21 wt % Ni-14 wt % Cr-0.5 wt % Mn-6 wt % Mo-2.5 wt % Nb-0.5 wt % Ta—Fe (balance). The wording "Co—Ni—Cr alloy" used herein is the conception including these Co—Ni—Cr alloys.

If a stainless steel is used as the material for forming the second wire 3, the pushability and torque transmission performance can be further enhanced.

The first wire 2 and the second wire 3 may be made from different alloys, and particularly, the first wire 2 is preferably made from a material having an elastic modulus smaller than that of the material of the second wire 3. With this configuration, the distal end portion of the guide wire 1A has a high flexibility, and the proximal end portion of the guide wire 1A has a high rigidity (flexural rigidity, torsional rigidity). As a result, the guide wire 1A has a high pushability and a high torque transmission performance, thereby enhancing the operationality, and also exhibits, on the distal side, a high flexibility and a high restoring performance, thereby improving trackability and safety to a blood vessel.

As one preferred combination of materials of the first wire 2 and the second wire 3, the first wire 2 is made from a superelastic alloy and the second wire 3 is made from a Co—Ni—Cr alloy or a stainless steel. With this configuration, the above-described effects become more significant.

In the configuration shown FIG. 1, the second wire 3 has a nearly constant outer diameter over the entire length; however, the second wire 3 may have portions with outer diameters changed in the longitudinal direction.

From the viewpoint of enhancing the flexibility and restoring performance of the distal end portion of the first wire 2, it is preferred to use a Ni—Ti alloy as the superelastic alloy for forming the first wire 2.

The coil 4 is a member formed by spirally winding a wire, particularly a fine wire, and is provided so as to cover the distal end portion of the first wire 2. In the configuration shown in FIG. 1, the distal end portion of the first wire 2 is disposed in an approximately axially center portion of the coil 4 in such a manner as to be not in contact with the inner surface of the coil 4. It is to be noted that in the configuration shown in FIG. 1, the coil 4 is loosely disposed in such a manner that a slight gap remains between adjacent spirally wound wire portions in a state that no external force is applied to the coil 4; however, the coil 4 may be tightly disposed in such a manner that no gap remains between the adjacent spirally wound wire portions in a state that no external force is applied to the coil 4.

The coil 4 may be made from a metal material such as a stainless steel, a superelastic alloy, a cobalt alloy, a noble metal such as gold, platinum, or tungsten, or an alloy containing such a noble metal. In particular, the coil 4 is preferably made from a radiopaque material such as a noble metal. If the coil 4 is made from such a radiopaque material, the guide wire 1A can exhibit an X-ray contrast performance. This makes it possible to insert the guide wire 1A in a living body while confirming the position of the distal end portion of the guide wire 1A under fluoroscopy. The distal side and proximal side of the coil 4 may be made from different alloys. For example, the distal side of the coil 4 may be formed of a coil made from a radiopaque material and the proximal side of the coil 4 be formed of a coil made from a relatively radiolucent material such as a stainless material. The entire length of the coil 4 is not particularly limited but may be in a range of about 5 to 500 mm.

The proximal end portion and the distal end portion of the coil 4 are fixed to the first wire 2 by a fixing material 11 and a fixing material 12, respectively, and an intermediate portion (close to the distal end) of the coil 4 is fixed to the first wire 2 by a fixing material 13. Each of the fixing materials 11, 12, and 13 is a solder (brazing material). Alternatively, each of the fixing materials 11, 12, and 13 may be an adhesive. In addition, in place of using the fixing material, the coil 4 may be fixed to the first wire 2 by welding. To prevent damage of the inner wall of a blood vessel, the leading end surface of the fixing material 12 is preferably rounded.

According to this embodiment, since the first wire 2 is partially covered with the coil 4, the contact area of the first wire 2 with the inner wall of a catheter used together with the guide wire 1A is small, with a result that it is possible to reduce the sliding resistance of the guide wire 1A in the catheter. This is effective to further improve the operationality of the guide wire 1A.

In this embodiment, the wire having a circular shape in cross-section is used for the coil 4; however, the cross-sectional shape of the wire used for the coil 4 may be another shape such as an elliptic shape or a quadrilateral shape (especially, rectangular shape).

In the guide wire 1A, the first wire 2 and the second wire 2 are joined to each other by welding. A welded portion (joining portion) 14 between the first wire 2 and the second wire 3 has a high joining strength.

In particular, according to the present invention, a projection 15 projecting in the outer peripheral direction is formed at the welded portion 14. The formation of such a projection 15 is effective to enlarge the joining area between the first wire 2 and the second wire 3, to significantly enhance the joining strength between the first wire 2 and the second wire 3. As a result, the guide wire 1A is advantageous in that the torsional torque and pushing force can be certainly transmitted from the second wire 3 to the first wire 2.

The formation of the projection 15 has another advantage in that the welded portion 14 between the first wire 2 and the second wire 3 may be easily visible under fluoroscopy. This may make it possible to easily, certainly recognize the advancing state of the guide wire 1A and a catheter in a blood vessel by checking the fluoroscopic image of the projection 15, and hence to shorten the operation time and improve the safety.

In the configuration shown in FIG. 1, each of one side (upper side) and the other side (lower side) of the projection 15 is formed into an approximately circular-arc shape in longitudinal cross-section, and the welded portion 14 is located at the maximum outer-diameter portion of the projection 15. With this configuration, the area of the welded surface of the welded portion 14 becomes large, to obtain a higher joining strength (welding strength). Another advantage is that when the guide wire 1A is bent, since the welded surface of the welded portion 14 is located at the maximum outer-diameter portion, stress is disconcentrated to a small outer-diameter portion closed to the projection 15. This makes it possible to prevent stress concentration at the welded portion 14. It is to be noted that according to the present invention, the shape of the projection 15 and the location of the welded portion 14 relative to the projection 15 are not limited to those described above.

As described above, the first wire 2 and the second wire 3 are generally made from materials having different elastic moduli. Accordingly, because of provision of the projection 15, an operator can easily, certainly, recognize a portion, at which the elastic modulus is relatively largely changed, of the guide wire 1A. This enhances the operationality of the guide wire 1A, to shorten the operation time and improve the safety.

The formation of the projection 15 has a further advantage in making small the contact area of the guide wire 1A with the inner wall of a catheter used together with the guide wire 1A, to reduce the sliding resistance of the guide wire 1A when the guide wire 1A is moved relative to the catheter, thus improving the sliding performance of the guide wire 1A. This enhances the operationality of the guide wire 1A in the catheter.

The height of the projection 15 is not particularly limited but is preferably in a range of 0.001 to 0.3 mm, more preferably, 0.01 to 0.05 mm. If the height of the projection 15 is less than the lower limit, it may fail to sufficiently obtain the above-described effects depending on the materials of the first wire 2 and the second wire 3. If the height of the projection 15 is more than the upper limit, since the inner diameter of a lumen, in which the guide wire 1A is to be inserted, of a balloon catheter is fixed, the outer diameter of the second wire 3 on the proximal side must be thin relative to the height of the projection 15, with a result that it may become difficult to ensure sufficient physical properties of the second wire 3.

In this embodiment, a connection end face 21 of the first wire 2 to the second wire 3 and a connection end face 31 of the second wire 3 to the first wire 2 are each formed into a plane nearly perpendicular to the axial (longitudinal) direction of both the wires 2 and 3. This significantly facilitates working for forming the connection end faces 21 and 31, to achieve the above-described effects without complicating the steps for producing the guide wire 1A.

It is to be noted that each of the connection end faces 21 and 31 may be tilted relative to the plane perpendicular to the axial (longitudinal) direction of both the wires 2 and 3, or formed into a recessed or raised shape.

The method of welding the first wire 2 and the second wire 3 to each other is not particularly limited but is generally exemplified by spot welding using laser or butt resistance welding such as butt seam welding. In particular, to ensure a high joining strength of the welded portion, butt resistance welding is preferable.

The procedure of joining the first wire 2 and the second wire 3 to each other by butt seam welding as one example of butt resistance welding will be described with reference to FIGS. 2A to 2C. FIGS. 2A to 2C show steps 1 to 3 of the procedure of joining the first wire 2 and the second wire 3 to each other by butt seam welding.

In the step 1, the first wire 2 and the second wire 3 are fixed (mounted) to a butt welder (not shown).

In the step 2, the connection end face 21 on the proximal side of the first wire 2 and the connection end face 31 on the distal side of the second wire 3 are butted to each other while a specific voltage is applied thereto by the butt welder. With this operation, a fused layer (welded surface) is formed at the contact portion, whereby the first wire 2 and the second wire 3 are strongly joined to each other. At this time, the projection 15 projecting in the outer peripheral direction is formed on the welded portion 14. The size (height) of the projection 15 can be controlled by adjusting, for example, an applied voltage and a pressing force applied between the first wire 2 and the second wire 3. Alternatively, the size (height) of the projection 15 may be adjusted, for example, by grinding.

In the step 3, the distal side of the first wire 2 is ground, to form the outer-diameter gradually reducing portion 16 with its outer-diameter gradually reduced in the direction toward the distal end.

Figure 3:
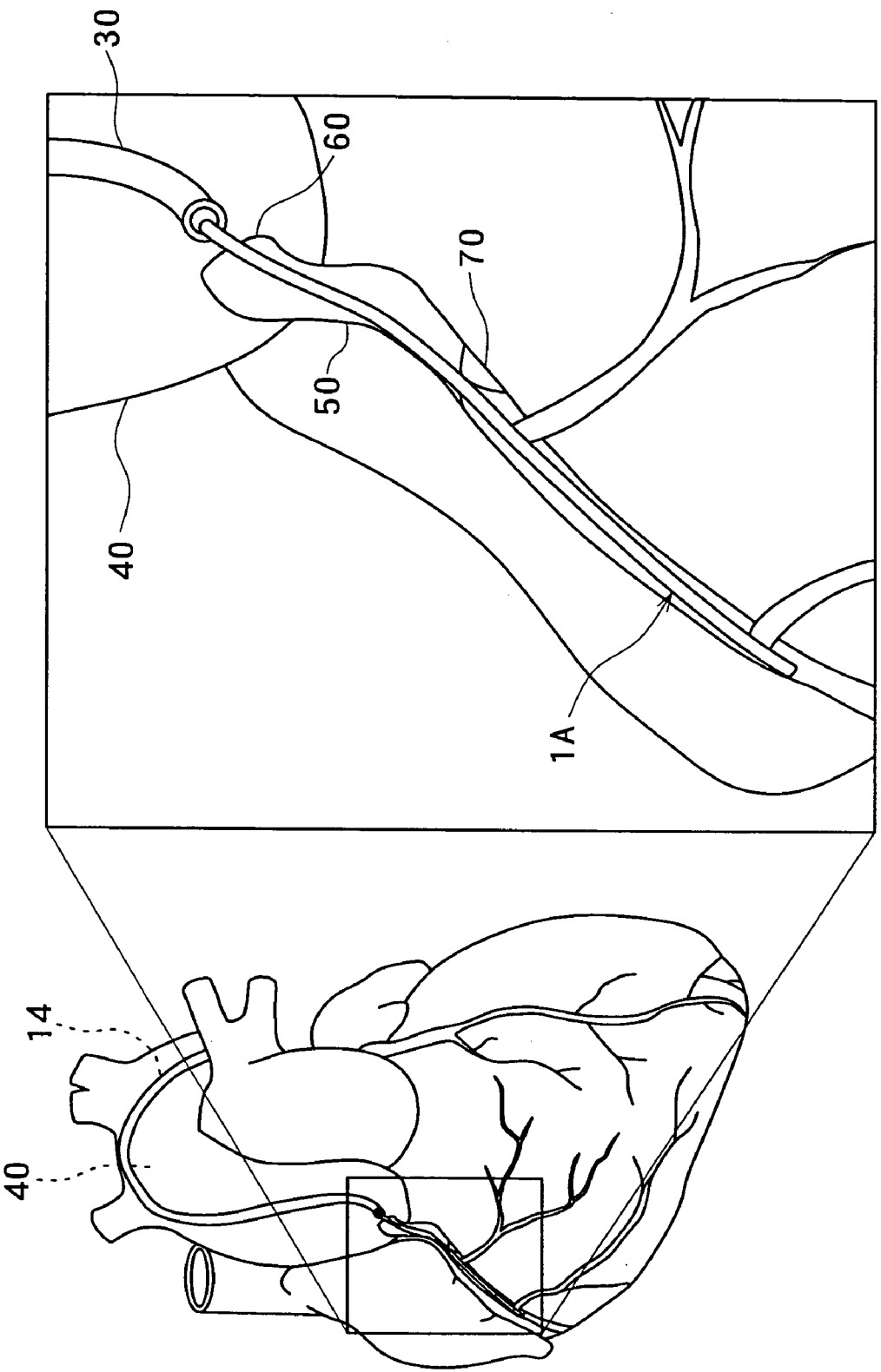
FIG. 3 is a typical view illustrating an example of how to use the guide wire of the present invention.
Figure 4:
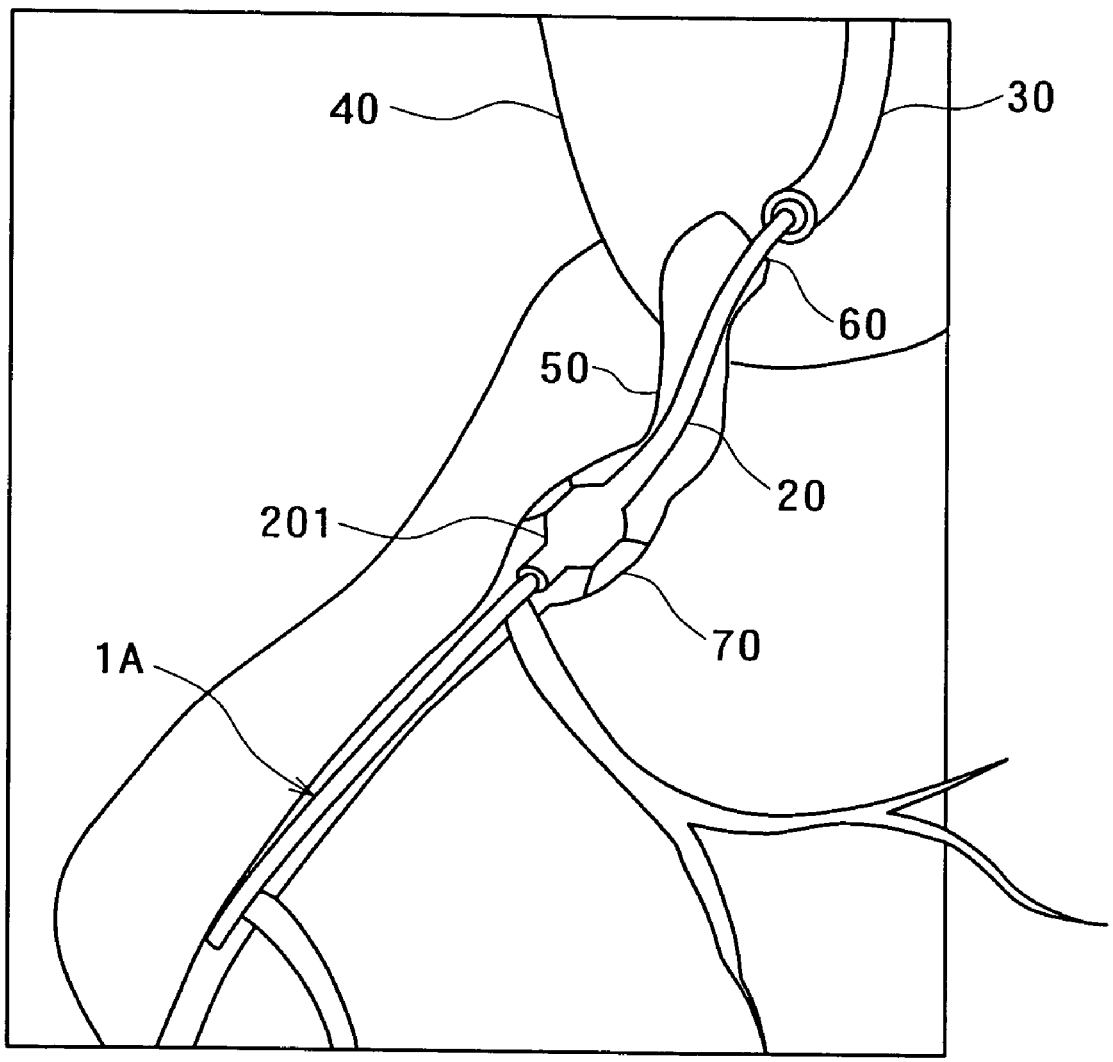
FIG. 4 is a typical view illustrating the example of how to use the guide wire of the present invention.

FIGS. 3 and 4 are views showing the operational state of the guide wire 1A of the present invention during use in the PTCA process.

In FIGS. 3 and 4, reference numeral 40 denotes an aortic arch, 50 is a right coronary artery of a heart, 60 is an ostium of the right coronary artery 50, and 70 is a target angiostenosis portion. Further, reference numeral 30 denotes a guiding catheter for certainly guiding the guide wire 1A from an arteria fermoralis into the right coronary artery 50, and 20 is a balloon catheter having at its distal end an expandable and contractible balloon 201 for dilating the target angiostenosis portion 70.

As shown in FIG. 3, the guide wire 1A is moved in such a manner that the distal end thereof projecting from the distal end of the guiding catheter 30 is inserted in the right coronary artery 50 through the ostium 60 of the right coronary artery 50. The guide wire 1A is further advanced, and is stopped when the distal end thereof passes the target angiostenosis portion 70 in the right coronary artery 50. In this state, an advance path of the balloon catheter 20 is ensured. At this time, the welded portion 14 of the guide wire 1A is located in the living body, more specifically, in the vicinity of the distal portion of the aortic arch 40.

As shown in FIG. 4, the balloon catheter 20 is inserted around the guide wire 1A from the proximal side of the guide wire 1A. The balloon catheter 20 is then advanced in such a manner that the distal end thereof projects from the distal end of the guiding catheter 30, goes ahead along the guide wire 1A, and enters the right coronary artery 50 from the ostium 60 of the right coronary artery 50. The balloon catheter 20 is stopped when the balloon 201 reaches a position corresponding to that of the target angiostenosis portion 70.

A fluid for inflating the balloon 201 is injected in the balloon catheter 20 from the proximal side of the balloon catheter 20, to inflate the balloon 201, thereby dilating the target angiostenosis portion 70. As a result, deposits such as cholesterol adhering on the arterial wall of the target angiostenosis portion 70 are physically compressed against the arterial wall, to eliminate blocking of blood flow.

Figure 5:
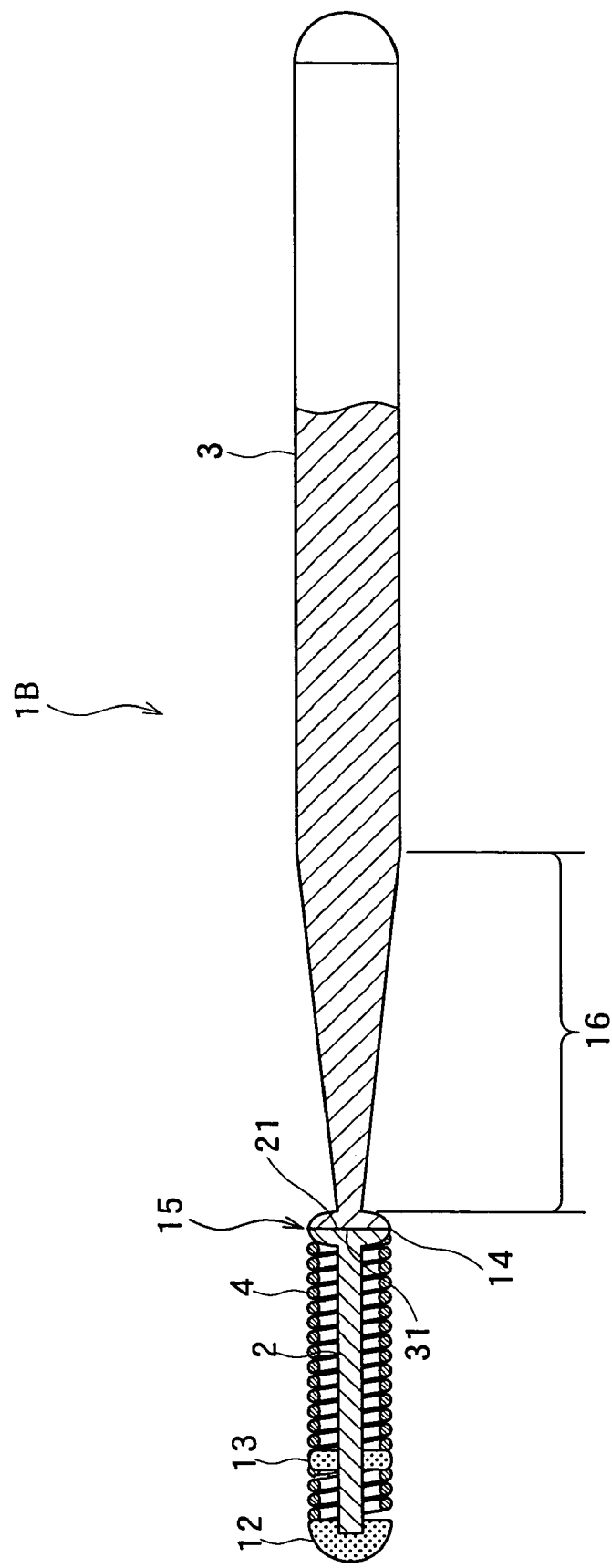
FIG. 5 is a longitudinal sectional view showing a second embodiment of the guide wire of the present invention.

FIG. 5 is a longitudinal sectional view showing a second embodiment of the guide wire of the present invention. The second embodiment of the guide wire of the present invention will now be described with reference to FIG. 5, principally, about differences from the previous embodiment, with the description of the same features omitted.

According to a guide wire 1B in this embodiment, an outer-diameter gradually reducing portion 16 is formed on a second wire 3, and a first wire 2 has an outer diameter being nearly constant nearly over the entire length except for a projection 15. In other words, in the guide wire 1B, the outer-diameter gradually reducing portion 16 is provided on the proximal side from the welded portion 14.

In the guide wire 1B, the proximal end of a coil 4 abuts on the projection 15.

Figure 6:
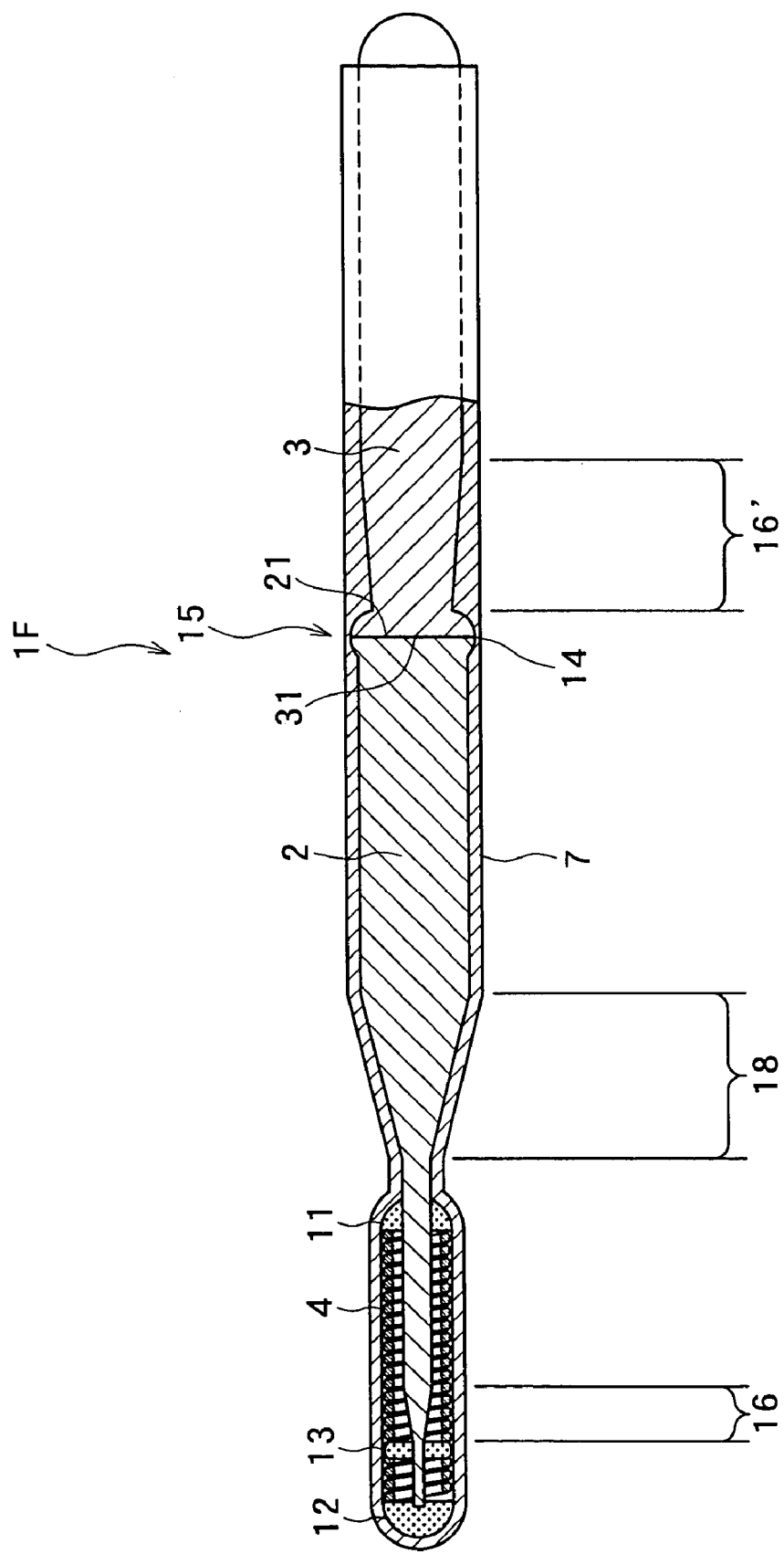
FIG. 6 is a longitudinal sectional view showing a third embodiment of the guide wire of the present invention.

FIG. 6 is a longitudinal sectional view showing a third embodiment of the guide wire of the present invention. The third embodiment of the guide wire of the present invention will now be described with reference to FIG. 6, principally, about differences from the previous embodiments, with the description of the same features omitted.

According to a guide wire 1F in this embodiment, a first wire 2 has an outer-diameter gradually reducing portion 16 and an outer-diameter gradually reducing portion 18 provided on the proximal side from the outer-diameter gradually reducing portion 16. In this way, according to the guide wire of the present invention, outer-diameter gradually reducing portions may be formed at a plurality of positions of the first wire 2 (or second wire 3).

In the guide wire 1F, the second wire 3 has an outer-diameter gradually reducing portion 16' located in the vicinity of the distal end. To be more specific, the second wire 3 has a first portion provided in the vicinity of the distal end and a second portion provided on the proximal side from the first portion, wherein the second portion has rigidity higher than that of the first portion. In the guide wire 1F, the first portion is configured as the outer-diameter gradually reducing portion 16'. This gives rise to an effect of smoothly changing transition of elasticity from the second wire 3 to the first wire 2. The first portion may be configured as a combination of the outer-diameter gradually reducing portion 16' and an outer-diameter constant portion provided on the distal side from the outer-diameter gradually reducing portion 16'. The outer-diameter constant portion preferably has a rigidity being nearly equal to that of the proximal portion of the first wire 2.

The guide wire 1F has a cover layer 7 on the outer surface (outer peripheral surface) side. In this way, the guide wire of the present invention may be configured to have a cover layer that covers the whole or part of the outer surface (outer peripheral surface). Such the cover layer 7 is formed for satisfying various purposes, one of which is to reduce the friction (sliding friction) of the guide wire 1F for improving the sliding performance of the guide wire 1F, thereby enhancing the operationality of the guide wire 1F.

To satisfy the above-described purpose, the cover layer 7 is preferably made from a material capable of reducing the friction of the guide wire 1F. With this configuration, since the friction resistance (sliding resistance) of the guide wire 1F against the inner wall of a catheter used together with the guide wire 1F is reduced, the sliding performance of the guide wire 1F is improved, to enhance the operationality of the guide wire 1F in the catheter. Further, since the sliding resistance of the guide wire 1F is reduced, it is possible to more certainly prevent, at the time of movement and/or rotation of the guide wire 1F in the catheter, kink (sharp bending) or torsion of the guide wire 1F, particularly, in the vicinity of a welded portion of the guide wire 1F.

Examples of the materials capable of reducing the friction of the guide wire 1F include polyorefins such as polyethylene and polypropylene, polyvinyl chloride, polyesters (such as PET and PBT), polyamide, polyimide, polyurethane, polystyrene, polycarbonate, silicone resins, fluorocarbon resins (such as PTFE and ETFE), silicone rubbers, various kinds of elastomers (for example, thermoplastic elastomers such as polyamide-based elastomer and polyester-based elastomer), and composite materials thereof. In particular, a fluorocarbon resin or a composite material thereof is preferable, and PTFE is more preferable.

According to this embodiment, a hydrophilic material or a hydrophobic material can be also used as another preferred example of the material capable of reducing the friction of the guide wire 1F. In particular, the hydrophilic material is preferable.

Examples of the hydrophilic materials include a cellulose based polymer, a polyethylene oxide based polymer, a maleic anhydride based polymer (for example, a maleic anhydride copolymer such as methylvinylether-maleic anhydride copolymer), an acrylic amide based polymer (for example, polyacrylic amide or polyglycidyl methacrylate-dimethyl acrylic amide [PGMA-DMAA] block copolymer), water-soluble nylon, polyvinyl alcohol, and polyvinyl pyrolidone.

In many cases, the hydrophilic material can exhibit a lubricating performance in a wet (water-absorbing) state. The use of the cover layer 7 made from such a hydrophilic material is effective to reduce the friction resistance (sliding resistance) of the guide wire 1F against the inner wall of a catheter used together with the guide wire 1F, to improve the sliding performance of the guide wire 1F, thereby enhancing the operationality of the guide wire 1F in the catheter.

The cover layer 7 may be formed in such a manner as to cover the whole or part of the guide wire 1F in the longitudinal direction. In particular, the cover layer 7 is preferably formed so as to cover a welded portion 14, and specifically, formed in a region including the welded portion 14.

The cover layer 7 covers the outer-diameter gradually reducing portion 16' and a projection 15 in such a manner as to have a substantially constant outer diameter. The wording "substantially constant outer diameter" used herein means an outer diameter that is smoothly changed to such a degree as not to cause any hindrance in use of the guide wire 1F.

The thickness (in average) of the cover layer 7 is not particularly limited but is preferably in a range of about 1 to 20 µm, more preferably, about 2 to 10 µm. If the thickness of the cover layer 7 is less than the lower limit, the effect obtained by formation of the cover layer 7 may be not sufficiently achieved and the cover layer 7 may be often peeled. If the thickness of the cover layer 7 is more than the upper limit, the physical properties of the wire may be obstructed and the cover layer 7 may be often peeled.

According to the present invention, the outer peripheral surface of the guide wire body (including the first wire 2, the second wire 3, and coil 4) may be subjected to a treatment (such as chemical treatment or heat treatment) for improving the adhesion characteristic of the cover layer 7, or may be provided with an intermediate layer for improving the adhesion characteristic of the cover layer 7.

The cover layer 7 may have a nearly constant composition or different compositions at respective portions. For example, the cover layer 7 may have a first region (first cover layer) for covering at least the coil 4 and a second region (second cover layer) on the proximal side from the first region, wherein the first cover layer and the second cover layer be made from different materials. Preferably, the first cover layer is made from a hydrophilic material and the second cover layer is made from a hydrophobic material. As shown in the figure, the first cover layer and the second layer may be formed so as to be continuous to each other in the longitudinal direction. Alternatively, the proximal end of the first cover layer may be separated from the distal end of the second cover layer, or the first cover layer may be partially overlapped to the second cover layer.

Such a cover layer (including the coating made from the hydrophilic material or the hydrophobic material) may be provided on the guide wire according to each of the first and second embodiments.

While the guide wire of the present invention has been described by way of the embodiments shown in the FIGS. 1 to 6, the present invention is not limited thereto. Each of the composing elements of the guide wire of the present invention may be replaced with a composing element having any other configuration exhibiting the similar effect, and may be provided with any other additional element.

For example, according to the guide wire of the present invention, projections projecting in the outer peripheral direction may be provided in addition to the above-described projection 15 provided at the welded portion 14.

Figure 7:
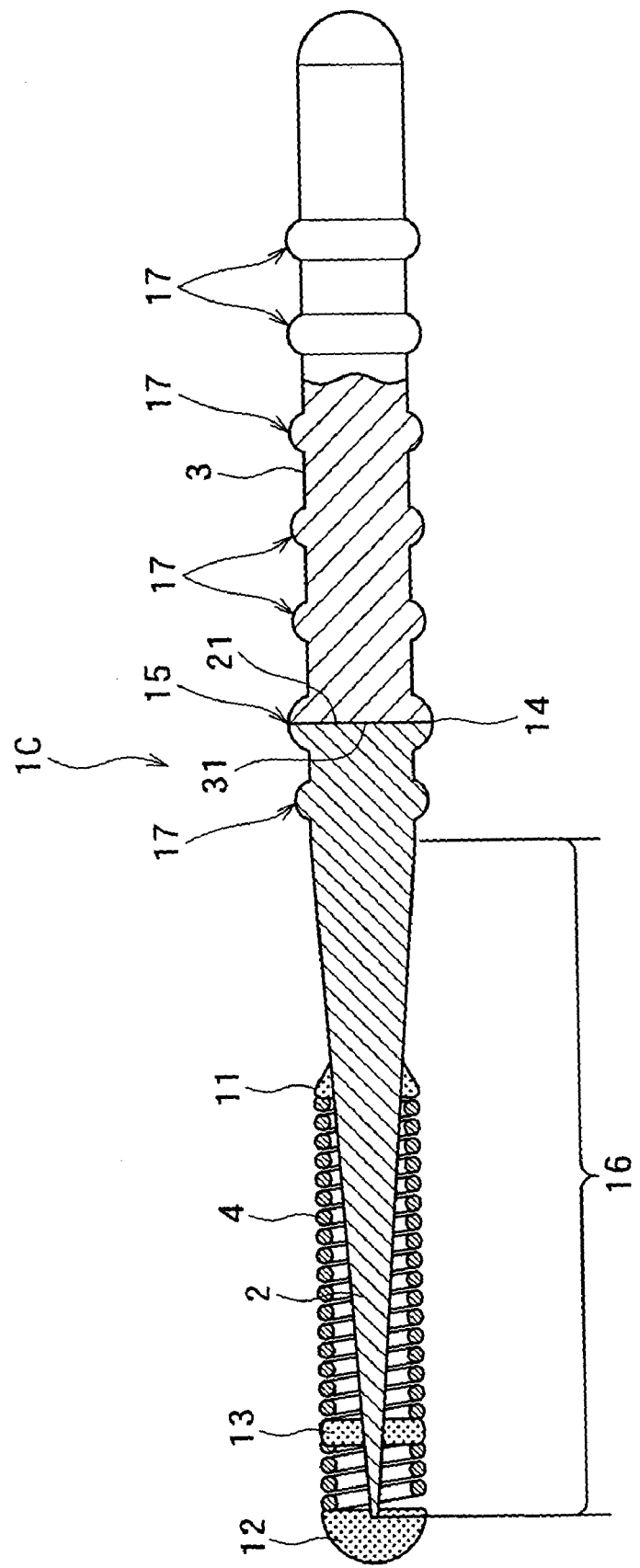
FIG. 7 is a longitudinal sectional view showing a modification of the guide wire of the present invention.
Figure 8:
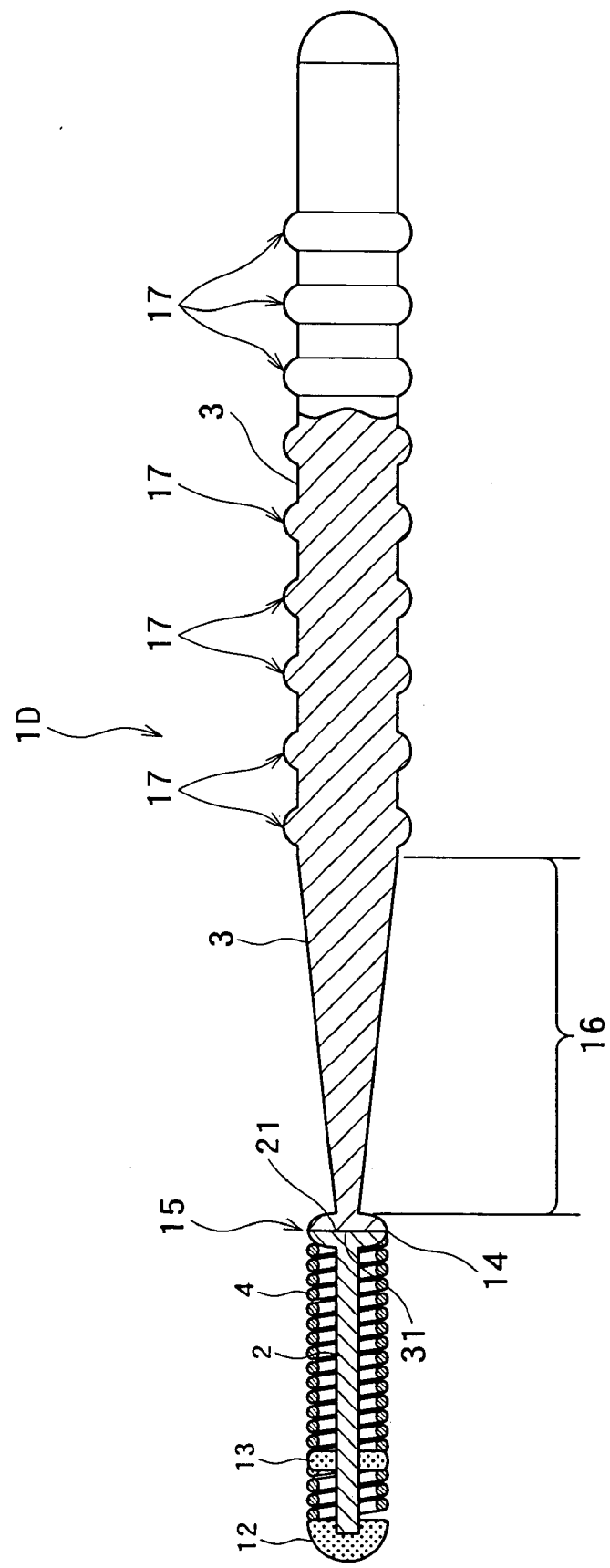
FIG. 8 is a longitudinal sectional view showing another modification of the guide wire of the present invention.

FIGS. 7 and 8 show such modifications of the guide wire of the present invention, in each of which projections 17 projecting in the outer peripheral direction are provided in addition to the projection 15 provided at the welded portion 14. The formation of these projections 17 is effective to further reduce the contact area of the guide wire with the inner wall of a catheter used together with the guide wire and hence to further reduce the friction resistance of the guide wire when the guide wire is moved relative to the catheter. This makes it possible to further improve the sliding performance of the guide wire and hence to further enhance the operationality of the guide wire in the catheter.

In the previous embodiments, the guide wire has the two wires, that is, the first wire 2 and the second wire 3, which are joined to each other only at one joining portion; however, the guide wire of the present invention may have two or more wires joined to each other at two or more joining portions. In other words, the guide wire of the present invention may have one or two wires other than the first wire 2 and the second wire 3.

Figure 9:
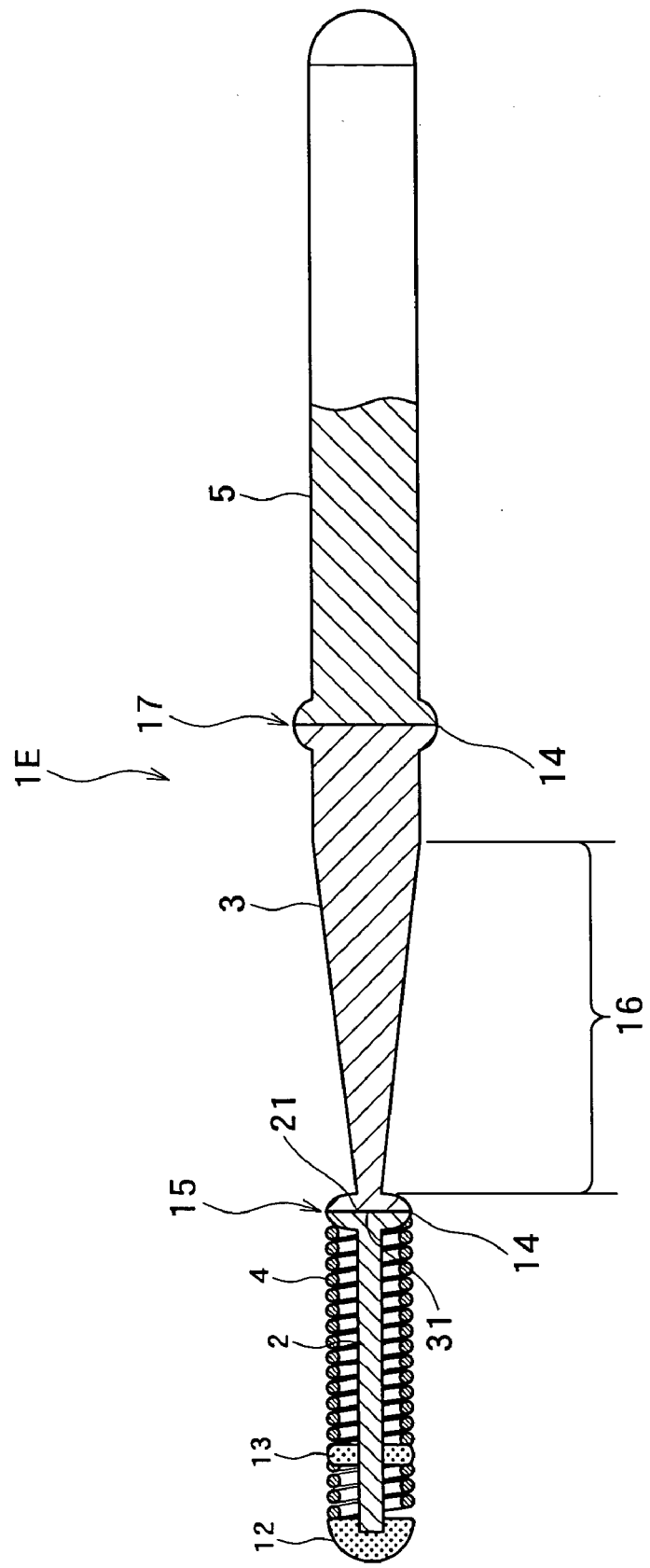
FIG. 9 is a longitudinal sectional view showing a further modification of the guide wire of the present invention.

FIG. 9 shows such a modification of the guide wire of the present invention. As shown in this figure, a guide wire 1E has a third wire 5 on the proximal side of the second wire 3. With this configuration, it is possible to more precisely set characteristics, such as elasticity, of respective portions of the guide wire in the longitudinal direction, and hence to further improve the operationality of the entire guide wire.

In this guide wire 1E, the second wire 3 is joined to the third wire 5 by means of a welded portion 14 similar to the welded portion 14 described in the previous embodiments. In this case, preferably, a projection 17 similar to the projection 15 described in the previous embodiments is formed on the welded portion 14.

In addition, although the welded portion 14 is located on the proximal side from the proximal end of the coil 4 in the previous embodiments, the welded portion 14 may be located on the distal side from the proximal end of the coil 4.

According to the present invention, the shape of the projection 15 or 17 formed on the welded portion 14 may be variously modified. Examples of the shapes of the projection 15 or 17 will be described below with respect to FIGS. 10 to 13.

Figure 10:
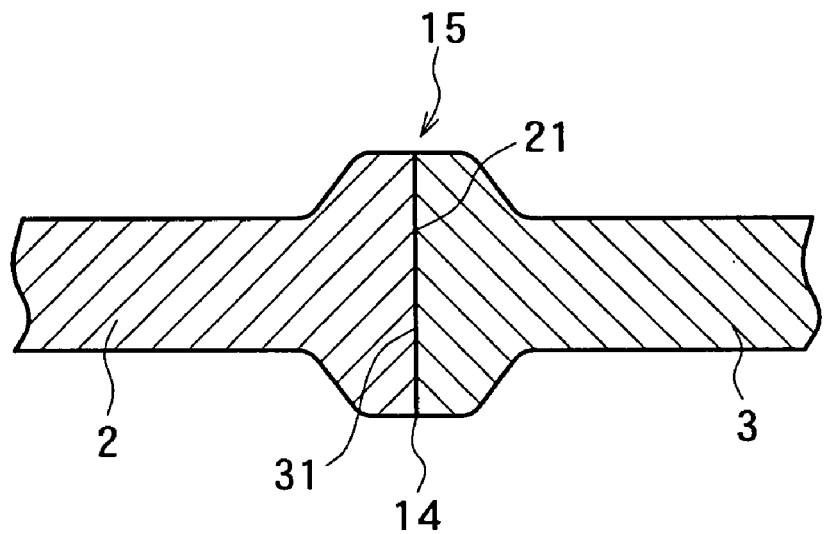
FIG. 10 is a longitudinal sectional view showing a modification of the shape of a projection of the guide wire of the present invention.

FIG. 10 shows one modification of the projection of the guide wire of the present invention. As shown in this figure, each of one side (upper side in the figure) and the other side (lower side in the figure) of a projection 15 is formed into a trapezoidal shape in longitudinal cross-section. In this way, according to the previous embodiments, each of the one side and the other side of the projection 15 is formed into an approximately circular-arc shape curved in a projecting manner in longitudinal cross-section; however, according to the present invention, each of the one side and the other side of the projection 15 may be formed into another shape, for example, a non-circular (non-circular arc) shape such as a trapezoidal shape or a triangular shape in longitudinal cross-section.

In the projection 15 shown in FIG. 10, a portion, in the vicinity of the welded portion 14, of the projection 15 (which portion is composed of two regions on the proximal side and the distal side from the welded portion 14, that is, which portion is equivalent to the upper base of the trapezoidal shape) has a nearly constant outer diameter. The welded portion 14 is located at a portion, having the maximum outer diameter, of the projection 15, and in this case, located at an approximately center of such a portion having a nearly constant outer diameter. With this configuration, it is possible to prevent or relieve stress concentration at the welded portion 14, and hence to more certainly prevent breakage of the welded portion 14 due to stress concentration at the welded portion 14 when a torsional torque or a pushing force is applied from the second wire 3 to the first wire 2.

The portion, having a nearly constant outer diameter, of the projection 15 may be replaced with a portion having a smooth circular-arc shape.

Figure 11:
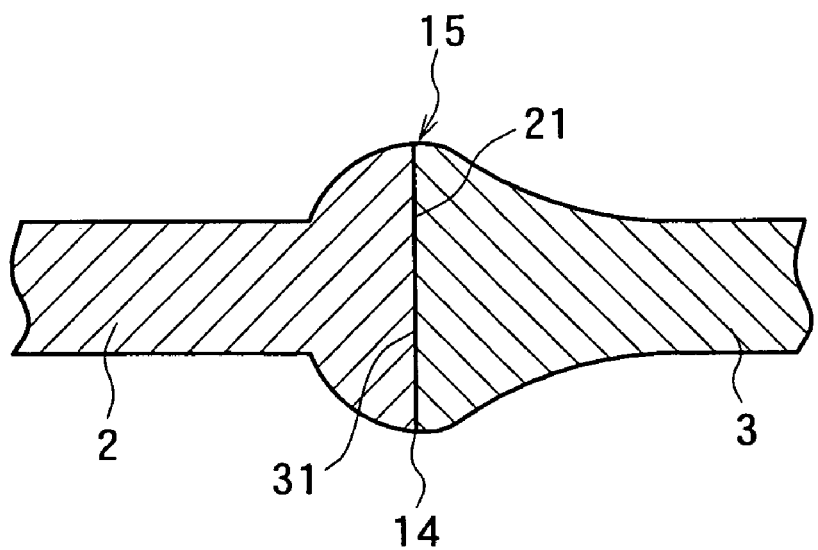
FIG. 11 is a longitudinal sectional view showing another modification of the shape of a projection of the guide wire of the present invention.
Figure 12:
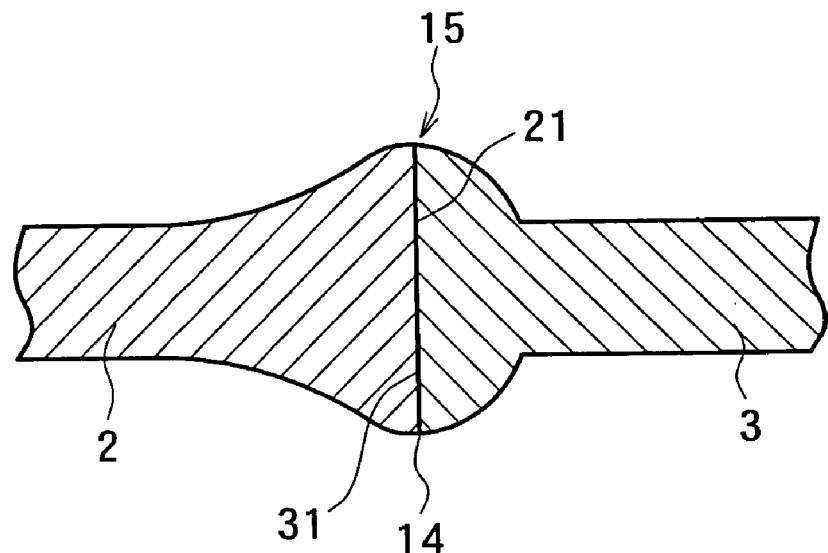
FIG. 12 is a longitudinal sectional view showing a further modification of the shape of a projection of the guide wire of the present invention.
Figure 13:
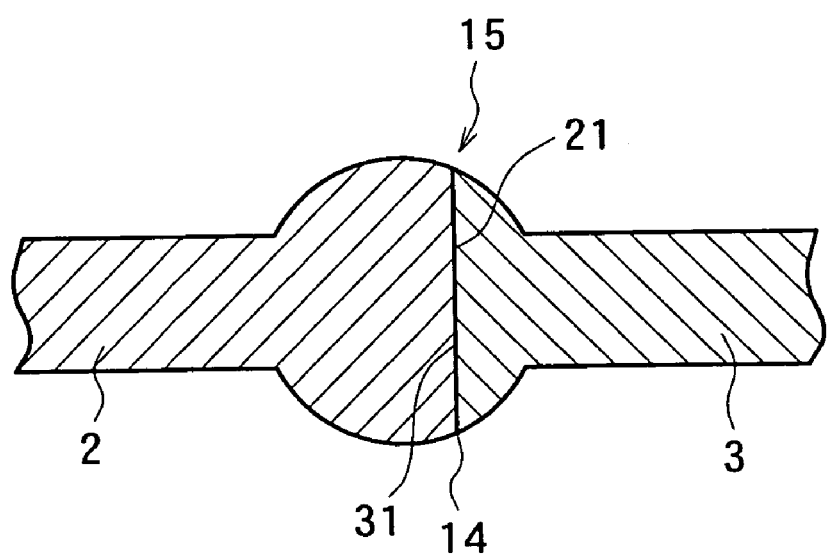
FIG. 13 is a longitudinal sectional view showing a further modification of the shape of a projection of the guide wire of the present invention.

FIGS. 11 to 13 show modifications of the projection of the guide wire of the present invention, in each of which the proximal side and the distal side of a projection are formed into shapes asymmetric to each other with respect to the welded surface (connection end face 21, 31) of the welded portion 14.

FIG. 11 shows another modification of the projection of the guide wire of the present invention. As shown in this figure, on the distal end (first wire 2 side) from the welded surface of the welded portion 14, each of one side (upper side) and the other side (lower side) of a projection 15 is formed into an approximately circular-arc shape in longitudinal cross-section which is similar to that described in each of the previous embodiments, whereas on the proximal side (second wire 3 side) from the welded surface of the welded portion 14, each of one side and the other side of the projection 15 is formed into a curved shape smoothly recessed in the direction from the welded portion 14 to the proximal end in longitudinal cross-section. In addition, the welded portion 14 is located at a portion, having the maximum outer diameter, of the projection 15.

With this configuration, it is possible to smoothen transition of rigidity and prevent or relieve stress concentration at the proximal end portion of the welded portion 14, and hence to more certainly prevent breakage, deformation, or the like of the proximal end portion of the welded portion 14 due to stress concentration when a torsional torque or a pushing force is applied from the second wire 3 to the first wire 2.

FIG. 12 shows a further modification of the projection of the guide wire of the present invention. A projection 14 according to this modification has a configuration reversed to that of the projection 15 shown in FIG. 11. As shown in this figure, on the proximal side (second wire 3 side) from the welded surface of the welded portion 14, each of one side (upper side) and the other side (lower side) of the projection 15 is formed into an approximately circular-arc shape in longitudinal cross-section which is similar to that described in the previous embodiments, whereas on the distal side (first wire 2 side) from the welded surface of the welded portion 14, each of one side and the other side of the projection 15 is formed into a curved shape smoothly recessed in the direction from the welded portion 14 to the proximal end in longitudinal cross-section. The welded portion 14 is located at a portion, having the maximum outer diameter, of the projection 15. The recessed curved shape in FIG. 11 and FIG. 12 may be replaced with a proximally constant taper shape.

With this configuration, it is possible to prevent or relieve stress concentration at the distal end portion of the welded portion 14, and hence to more certainly prevent breakage, deformation, or the like of the distal end portion of the welded portion 14 due to stress concentration when a torsional torque or a pushing force is applied from the second wire 3 to the first wire 2.

Of course, on each of the distal side and the proximal side from the welded surface of the welded portion 14, each of the one side and the other side of the projection 15 may be formed into a curved shape smoothly recessed in the direction separating from the welded portion 14 in longitudinal cross-section.

FIG. 13 shows a further modification of the projection of the guide wire of the present invention. As shown in this figure, a projection 15 is formed into an approximately circular-arc shape similar to that described in the previous embodiments as a whole; however, in this projection 15, the welded surface of the welded portion 14 is offset to the proximal side (second wire 3 side). Reversely, in this projection 15, the welded surface of the welded portion 14 may be offset to the distal side (first wire 2 side).

With this configuration, since the welded surface of the welded portion 14 is not located at a central portion of the projection 15 in the axial direction, that is, it is out of the maximum outer-diameter portion of the projection 15, it is possible to prevent or relieve stress concentration at the welded portion 14, and hence to more certainly prevent breakage of the welded portion 14 due to stress concentration at the welded portion 14 when a torsional torque or a pushing force is applied from the second wire 3 to the first wire 2.

The configuration that in the projection 15, the welded surface of the welded portion 14 is offset onto the proximal side or the distal side may be applied, for example, to the configuration that each of one side and the other side of the projection 15 is formed into a non-circular (non-circular arc) shape in longitudinal cross-section as shown in FIG. 10.

As described above, by making the shapes of the proximal side and the distal side of the projection 15 asymmetric to each other with respect to the welded surface of the welded portion 14, it is possible to prevent or relieve stress concentration at the welded portion 14, and to more certainly prevent breakage of the welded portion due to stress concentration at the welded portion 14 when a torsional torque or a pushing force is applied from the second wire 3 to the first wire 2.

Figure 14:
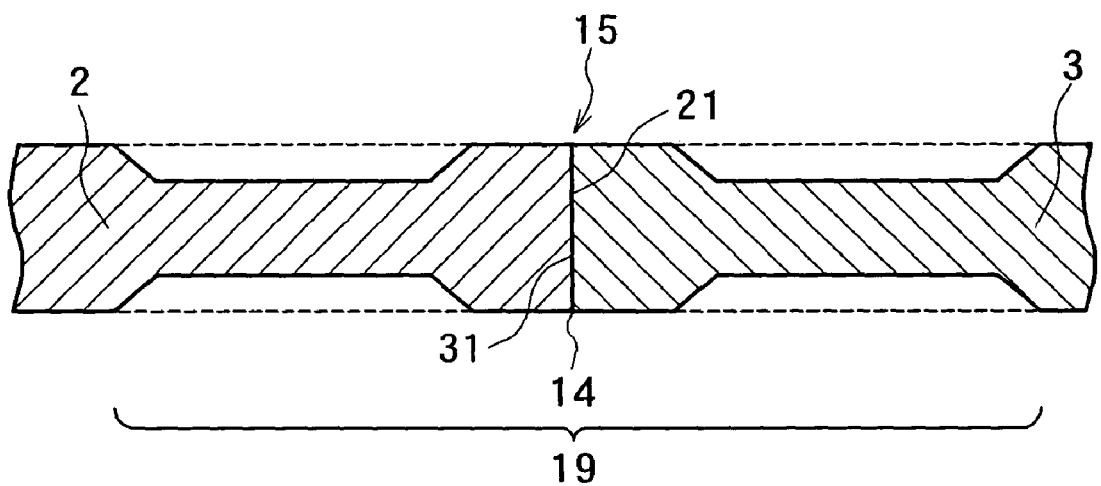
FIG. 14 is a longitudinal sectional view showing a modification of the shape of portion, in the vicinity of a welded portion, of the guide wire of the present invention.

FIG. 14 shows a further modification of a portion, in the vicinity of the welded portion, of the guide wire of the present invention. As shown in this figure, a portion, in the vicinity of a joining portion (welded portion 14) between the first wire 2 and the second wire 3, of the guide wire is thinner than the remaining portion, and a welded portion 14 and a projection 15 are formed in a mid portion of a thinned portion 19 in the longitudinal direction.

With this configuration, it is possible to prevent or relieve stress concentration at the welded portion 14, and hence to more certainly prevent breakage of the welded portion 14 due to stress concentration at the welded portion 14 when a torsional torque or a pushing force is applied from the second wire 3 to the first wire 2.

Preferably, the maximum outer diameter of the projection 15 is equal to or less than the outer diameter of a portion on the proximal side or distal side from the thinned portion 19. This is effective to further smoothen movement of the guide wire relative to a catheter.

In the configuration shown in FIG. 14, the shape of the projection 15 is nearly equal to that shown in FIG. 10; however, the shape of the projection 15 may be either of the shapes shown in FIG. 1 and FIGS. 5 to 13.

The configuration of each of the modifications shown in FIGS. 11 to 14 may be applied to either of the first, second, and third embodiments. In particular, the configuration of each of the modifications shown in FIGS. 11 to 14 may be applied to the projection 17 described in the third embodiment shown in FIG. 6.

While the preferred embodiments of the present invention have been described using specific terms, such description is for illustrative purposes only, and it is to be understood that changes and variations may be made without departing from the spirit or scope of the following claims.

The entire disclosure of Japanese Patent Application No. 2002-244316 filed on Aug. 23, 2002, Japanese Patent Application No. 2002-355907 filed on Dec. 6, 2002 and Japanese Patent Application No. 2003-156010 filed on May 30, 2003 including specification, claims, drawings, and summary are incorporated herein by reference in its entirety.

What is claimed is:

1. A guide wire comprising:
a first wire disposed on the distal side of said guide wire;
a second wire disposed on the proximal side from said first wire;
wherein said first wire and said second wire are joined to each other by welding;
a welded portion formed by the welding has a projection projecting in the outer peripheral direction;
the projection extending on both axial sides of the welded portion;
said first wire and said second wire are not helical coils;
the proximal side and the distal side of said projection are formed into shapes asymmetric to each other with respect to the welded surface of said welded portion;
a spiral coil covering at least a distal end portion of said first wire; and
material forming at least one of the proximal end of the first wire and the distal end of the second wire constitutes at least a part of the projection.

2. A guide wire according to claim 1, wherein said projection is visible under fluoroscopy.

3. A guide wire according to claim 1, wherein the proximal end of said coil abuts on said projection.

4. A guide wire according to claim 1, wherein the vicinity of said welded portion between said first wire and said second wire, has a thinned portion, and said projection is provided on said thinned portion.

5. A guide wire according to claim 1, further comprising a cover layer covering the projection.

6. A guide wire comprising:
a first wire disposed on the distal side of said guide wire;
a second wire disposed on the proximal side from said first wire;
the first wire is made of a pseudo-elastic alloy and the second wire is made of a different material than the first wire;
the second wire possessing an elasticity modulus greater than the elasticity modulus of the first wire;
wherein said first wire and said second wire are joined to each other by welding;
a welded portion formed by the welding has a projection projecting in the outer peripheral direction;
the projection extending on both axial sides of the welded portion;
the proximal side and the distal side of said projection are formed into shapes asymmetric to each other with respect to the welded surface of said welded portion;
the first wire and said second wire are not helical coils;
a welded surface of the welded portion at which the first and second wires are welded to each other being located at a maximum outer-diameter portion of the projection to disconcentrate stress to a smaller outer-diameter portion close to the projection;
a spiral coil covering at least a distal end portion of said first wire; and
material forming at least one of the proximal end of the first wire and the distal end of the second wire constitutes at least a part of the projection.

7. A guide wire according to claim 6, wherein the spiral coil does not cover the projection.

8. A guide wire according to claim 6, wherein the spiral coil possesses a proximal-most end positioned on a distal side of the projection.

9. A guide wire according to claim 6, wherein the projection is not surrounded by a spiral wire.

10. A guide wire according to claim 6, further comprising a cover layer covering the projection.

11. A guide wire according to claim 10, wherein the projection possesses an outer peripheral surface, the cover layer directly contacting the outer peripheral surface of the projection.

12. A guide wire comprising:
a first wire disposed on the distal side of said guide wire;
a second wire disposed on the proximal side from said first wire;
wherein said first wire and said second wire are joined to each other by welding;
a welded portion formed by the welding has a projection projecting in the outer peripheral direction;
the projection extending on both axial sides of the welded portion;
the projection possessing an outer peripheral surface;
the proximal side and the distal side of said projection are formed into shapes asymmetric to each other with respect to the welded surface of said welded portion;

a cover layer in direct contact with the outer peripheral surface of the projection to cover the projection;
the cover layer being a friction-reducing polymer material;
said first wire and said second wire are not helical coils;
a spiral coil covering at least a distal end portion of said first wire; and
material forming at least one of the proximal end of the first wire and the distal end of the second wire constitutes at least a part of the projection.

13. A guide wire according to claim 12, wherein the spiral coil possesses a proximal-most end positioned on a distal side of the projection.

14. A guide wire according to claim 12, wherein the spiral coil does not cover the projection.

15. A guide wire according to claim 12, wherein the projection is not surrounded by a spiral wire.

16. A guide wire according to claim 12, wherein the cover layer possesses an uncovered outer surface so that the cover layer is an outermost surface of at least a part of the guide wire.

17. A guide wire comprising:
a first wire disposed on the distal side of said guide wire;
a second wire disposed on the proximal side from said first wire;
wherein said first wire and said second wire are joined to each other by welding;
a welded portion formed by the welding has a projection projecting in the outer peripheral direction;
the projection extending on both axial sides of the welded portion;
the projection possessing an outer peripheral surface;
the proximal side and the distal side of said projection are formed into shapes asymmetric to each other with respect to the welded surface of said welded portion;
said first wire and said second wire are not helical coils;
a spiral coil covering at least a distal end portion of said first wire;
the spiral coil does not cover the projection,
the projection is not covered by a spiral-shaped wire; and
material forming at least one of the proximal end of the first wire and the distal end of the second wire constitutes at least a part of the projection.

18. A guide wire according to claim 17, the first wire is made of a pseudo-elastic alloy and the second wire is made of a different material than the first wire so that the second wire possesses an elasticity modulus greater than the elasticity modulus of the first wire.

19. A guide wire according to claim 17, further comprising a cover layer covering the projection.

20. A guide wire according to claim 19, wherein the cover layer possesses an uncovered outer surface so that the cover layer is an outermost surface of at least a part of the guide wire.

21. A guide wire comprising:
a first wire disposed on the distal side of said guide wire;
a second wire disposed on the proximal side from said first wire;
wherein said first wire and said second wire are joined to each other by welding at a weld joint so as to define a first enlarged proximal-most end portion of the first wire and a first enlarged distal-most end portion of the second wire;
a projection formed by said welding and projecting in an outer peripheral direction on both axial sides of the weld joint, said projection defining a final enlarged proximal-most end portion of the first wire and a final enlarged distal-most end portion of the second wire forming a smooth joining surface therebetween;
wherein the final enlarged proximal-most end portion of the first wire portion does not extend farther radially outwardly than said first enlarged proximal-most end portion of the first wire and the final enlarged distal-most end portion of the second wire does not extend farther radially outwardly than said first enlarged distal-most end portion of the second wire;
said first wire and said second wire are not helical coils;
a spiral coil covering at least a distal end portion of said first wire; and
material forming at least one of the proximal end of the first wire and the distal end of the second wire constitutes at least a part of the projection.

22. A guide wire according to claim 21, further comprising a cover layer covering the projection.

23. A guide wire according to claim 21, wherein the proximal end of said coil abuts on said projection.

24. A guide wire according to claim 21, wherein the proximal side and the distal side of said projection are formed into shapes asymmetric to each other with respect to the welded surface of said welded portion.

25. A guide wire according to claim 21, wherein said projection is visible under fluoroscopy.

* * * * *